(12) United States Patent
Wendelstorf et al.

(10) Patent No.: US 7,455,665 B2
(45) Date of Patent: *Nov. 25, 2008

(54) HYGIENE ARTICLE WITH FASTENING ELEMENTS

(75) Inventors: Carsten Wendelstorf, Ulm (DE); Rainer Mangold, Herbrechtingen (DE)

(73) Assignee: Paul-Hartmann AG, Heidenheim (DE)

( * ) Notice: Subject to any disclaimer, the term of this patent is extended or adjusted under 35 U.S.C. 154(b) by 137 days.

This patent is subject to a terminal disclaimer.

(21) Appl. No.: 10/486,315

(22) PCT Filed: Jun. 24, 2002

(86) PCT No.: PCT/EP02/06946

§ 371 (c)(1),
(2), (4) Date: Feb. 9, 2004

(87) PCT Pub. No.: WO03/015675

PCT Pub. Date: Feb. 27, 2003

(65) Prior Publication Data

US 2004/0236301 A1  Nov. 25, 2004

(30) Foreign Application Priority Data

Aug. 18, 2001  (DE) ............................. 101 40 622

(51) Int. Cl.
*A61F 13/15* (2006.01)
(52) U.S. Cl. .................................. 604/385.03; 604/387
(58) Field of Classification Search ............ 604/385.03, 604/386, 387, 389, 391
See application file for complete search history.

(56) References Cited

U.S. PATENT DOCUMENTS

| 4,177,812 A | * | 12/1979 | Brown et al. ................. 604/390 |
| 4,237,890 A | * | 12/1980 | Laplanche ................... 604/390 |
| 4,576,598 A | * | 3/1986 | Tritsch ........................ 604/390 |
| 4,670,012 A | * | 6/1987 | Johnson ...................... 604/390 |
| 5,234,517 A | | 8/1993 | Pape et al. |
| 5,591,521 A | * | 1/1997 | Arakawa et al. ............. 428/352 |
| 5,624,428 A | * | 4/1997 | Sauer ......................... 604/391 |
| 5,624,429 A | | 4/1997 | Long et al. |
| 6,030,373 A | | 2/2000 | VanGompel et al. |

(Continued)

FOREIGN PATENT DOCUMENTS

DE  298 21 530  2/1999

(Continued)

*Primary Examiner*—Tatyana Zalukaeva
*Assistant Examiner*—Michael G Bogart
(74) *Attorney, Agent, or Firm*—YoungBasile (57) ABSTRACT

A hygiene article has a fluid permeable protective layer, a rear, fluid impermeable layer and an absorbing body arranged between the layers. The article has a first longitudinal direction and a second transverse direction. Fastening elements are provided for removably fastening the hygiene article when worn by a user. The fastening elements include a clip which cooperates with an application zone of the hygiene article. Each fastening element has a first zone, by means of which the fastening element can be attached to the hygiene article, and a second zone, arranged at a distance from the first zone in the transverse direction and in which the clip is provided. Each fastening element is folded in a zigzag manner along folding lines extending in the longitudinal direction. The second zone provided with the clip is arranged outside of the zigzag folded configuration in the transverse direction.

31 Claims, 4 Drawing Sheets

U.S. PATENT DOCUMENTS

| | | | |
|---|---|---|---|
| 6,039,906 A * | 3/2000 | Sageser et al. | 264/156 |
| 6,142,986 A | 11/2000 | Lord et al. | |
| 6,363,587 B1 * | 4/2002 | Richter et al. | 24/306 |
| 6,524,294 B1 * | 2/2003 | Hilston et al. | 604/386 |
| 6,562,631 B2 * | 5/2003 | Braach-Maksvytis et al. | 436/518 |
| 6,656,171 B1 * | 12/2003 | Matsuda et al. | 604/390 |
| 2004/0194260 A1 * | 10/2004 | Wendelstorf et al. | 24/442 |
| 2005/0143709 A1 * | 6/2005 | Lindstrom | 604/391 |

FOREIGN PATENT DOCUMENTS

| | | |
|---|---|---|
| DE | 200 05 920 | 6/2000 |
| EP | 0 669 121 | 8/1995 |
| EP | 0 832 631 | 4/1998 |
| EP | 0 951 888 | 10/1999 |
| EP | 1 062 931 | 12/2000 |
| FR | 2 267 058 | 11/1975 |
| FR | 1 151 736 | 11/2001 |
| GB | 1 441 567 | 7/1976 |
| WO | WO 98/22069 | 5/1998 |
| WO | WO 99/33425 | 8/1999 |

* cited by examiner

HYGIENE ARTICLE WITH FASTENING ELEMENTS

BACKGROUND

The invention relates to a hygiene article, also particularly a diaper for incontinence, having a fluid-pervious top sheet, a fluid-impervious back sheet and an absorbent core disposed therebetween, and having fastening elements for releasably closing the hygiene article when applied to the user.

Hygiene articles with fastening elements folded over on themselves prior to use are known, for example, from EP 0 669 121 A1 or WO 95/16425. Fastening elements folded over on themselves in a Z-shape for disposable hygiene articles are also known from U.S. Pat. No. 4,237,890

SUMMARY

Based on this prior art, the object of the present invention is to improve a hygiene article of this type with respect to ease of attachment of the fastening elements during manufacture of the hygiene article, but also to simplify the handling of the hygiene article after the fastening elements are attached in a high-speed production machine and during a subsequent packaging process. A further object of the present invention is to improve the manageability of the hygiene article during unfolding, positioning and closing of the fastening elements when the hygiene article is attached to a user.

This object is achieved by a hygiene article of the type described in accordance with the invention by placing the second zone having the securing means outside the folded, Z-shaped configuration in the transverse direction.

The present invention accordingly proposes to fold the fastening element in the longitudinal direction in such a way that the result is a Z-shaped configuration, of which one part, or section, of the fastening element which has the second zone with the securing means projects transversely, is thus located outside the folded, Z-shaped configuration. In this way it is possible to affix, i.e. to attach, the particular fastening element with its first zone on a surface of the hygiene article. The part or section of the fastening element projecting at the side, in the transverse direction from the folded Z-shaped configuration, can now be grasped easily under the invention. Since the gummy or otherwise adhesively configured securing means is furnished there, advantages also accrue with respect to manufacture; the securing means is prevented from interfering in a distracting fashion with the folded, Z-shaped configuration.

In a further aspect of the invention, the particular fastening element with a zone lying outside the folded, Z-shaped configuration forms a releasable retentive connection with the top side of the hygiene article by providing adhesive or retaining means. For example, the second section of the fastening element could have spots of glue at any location which adhere to the top side of the hygiene article in an easily releasable manner and thus retain the fastening element in the intended assembled position. It would also be conceivable that the second zone, which has the active securing means, is overlaid with a detachable covering which in turn has an adhesive coating to releasably retain the section to the top side of the hygiene article.

However, in a further aspect of the invention it is proposed that the releasable retentive connection is formed by the securing means in the second zone of the fastening element itself.

It also proves to be advantageous if the particular securing means is formed by mechanically acting closures. To create a releasable retentive connection, the closures can coact with a textile-like top side of the hygiene article, for example, in the manner of a hook-and-loop material.

With respect to the attachment of the fastening elements to the hygiene article, an arrangement on the inner user facing side, that is, on the side of the fluid-pervious top sheet, could be considered, or an attachment by means of fork-shaped or Y-shaped retaining tabs, which clasp the combined top sheet and back sheet of the hygiene article from both sides and are attached there. However, in embodying the present invention, it proves to be particularly advantageous if the fastening elements are attached to a side of the hygiene article facing away from the body.

The side facing away from the body can advantageously have a textile-like surface. This textile-like surface advantageously comprises the fluid-impervious back sheet and can be made from a nonwoven-plastic film laminate. In this embodiment it is possible to implement the releasable retentive connection through mechanically acting closures which are located outside the folded, Z-shaped configuration and coact directly with the textile-like surface in an adherent manner.

In accordance with a further aspect of the invention, the folded, Z-shaped fastening elements are spaced apart in the transverse direction from a longitudinal edge of the hygiene article in such a way that the second zone with the securing means is located at least almost entirely inside the longitudinal edge. This is intended to convey that the second zone with the securing means should protrude as little as possible, preferably not at all, beyond the longitudinal edge of the hygiene article. This is to prevent the protruding area of the securing means from catching on the top sheet when the hygiene article is folded onto the body facing top sheet and damaging said top sheet when it is detached. The second zone should not protrude outwardly more than 5 mm, preferably less than 3 mm, most specifically less than 2 mm in the transverse direction beyond the longitudinal edge. The side sections of the rear area of the hygiene article, often described as "ears" and carrying the fastening elements, are folded in on the body facing top sheet as part of the folding of the hygiene article during manufacture. This prevents the particular securing means from becoming entangled with the surface of the normally fleecy top sheet and damaging said top sheet. Furthermore, fleecy material could become stuck on the securing means and negatively affect the closing ability of the mechanically acting closures.

In a further aspect of the invention it is proposed to configure the fastening elements in such a way that a pull tab is furnished for the user to take hold of with a finger. The pull tab is furnished in the transverse direction outside the second zone of the particular fastening element and on the side of the second zone facing away from the folded, Z-shaped configuration.

In yet another aspect of this inventive concept, the fastening element is positioned on the surface of the hygiene article facing away from the body and attached there in such a way that its pull tab protrudes beyond a longitudinal edge of the hygiene article in the transverse direction. This proves to be advantageous insofar as with the hygiene article spread out and unfolded, the particular fastening element with its pull tab projects in the transverse direction beyond the longitudinal edges of the hygiene article on both sides and are thus visible. The tabs can then be easily grasped by a user's fingers, who takes hold of the pull tab with one hand, and with the other hand, perhaps with thumb and forefinger, takes holds of a longitudinal edge area of the hygiene article and then exerts a pulling motion. The releasable retentive connection between the fastening element and the surface of the diaper is thereby broken and the folded, Z-shaped configuration is unfolded, so that the fastening element can be moved in a direction encircling the hips towards the contact zone provided in the front area of the hygiene article, to be secured there to close the hygiene article when applied to a user.

The particular fastening element can have a first section of a first supporting layer and a second section of a second supporting layer which is disposed in the transverse direction next to the first section and is connected thereto. The first section has the first zone and the second section has the second zone.

It proves to be advantageous if a fold line of the fastening element running in the longitudinal direction runs at least in sections along a material transition between the first and second section of the fastening element. The ability of the fastening element to be folded is thereby improved, and the thickness of the folded, Z-shaped configuration is kept as small as possible.

Preferably the fold line runs immediately along a longitudinal edge of the second section of the fastening element.

The first and the second section of the particular fastening element can be joined in any way whatsoever, i.e., they could butt against each other and be overlaid by a third, specifically strip-shaped, fastening element which joins the two sections non-detachably. It is also conceivable and advantageous for the first and the second section of the fastening element to be overlapped in the transverse direction and be joined in the overlap area. In this case, it proves advantageous if a fold line of the fastening element running in the longitudinal direction runs immediately along a longitudinal edge of the first zone.

In a further aspect of the invention, it proves advantageous if a further fold line of the folded, Z-shaped configuration runs immediately along a longitudinal edge of an adhesive coating in the first zone. The adhesive coating of the first zone can be of any extent, where to achieve very good securing of the folded, Z-shaped configuration on the top side of the hygiene article, as extensive an application of adhesive as possible, specifically delineated as a rectangle in plan view, is recommended.

It furthermore proves advantageous if the second supporting layer of the fastening element comprises an essentially inelastic material and is essentially not extensible in the transverse direction. In contrast, it is proposed that the first supporting layer of the fastening element comprises a material essentially extensible at least in the transverse direction and is configured elastically extensible in this transverse direction.

As used herein, elastically extensible refers to a material which can be stretched by at least 1.2 times its original dimension when tension is applied and, when tension is removed, contracts again at least far enough to nullify at least half of the stretched length. Of course, materials are known and preferred for use as the first supporting layer which demonstrate much more pronounced retraction characteristics.

To achieve these elastically extensible properties for the first supporting layer, elastic nonwovens or so-called "stretchbond" laminates with one or more nonwoven and/or plastic film layers can be employed.

In a further aspect of the inventive concept, it is proposed to secure the folded, Z-shaped configuration of the fastening element releasably to itself. This can be achieved, for example, by securing the folded, Z-shaped configuration with a plurality of 1 to 10, preferably 3 to 5 discrete attachment points, such as weld spots, with a cross-sectional area of less than 1 mm$^2$, so that the folded, Z-shaped configuration is prevented from unfolding during the manufacturing or packaging process or before the hygiene article is unfolded as intended when it is applied.

It was ascertained in a further development of this inventive concept that the folded, Z-shaped configuration can also be secured to itself when longitudinal sections forming a particular fastening element are severed from a continuous web in the transverse direction; fibers from the layers folded over on each other in a Z-shape are worked or pulled into the layer disposed thereunder at the cut edge thus created. So when these longitudinal sections are severed, a type of needling effect in fibrous nonwovens can be achieved, which is sufficient to hold the folded, Z-shaped configuration to itself When the longitudinal sections are severed, particularly if a "crush cut" is made, fibers from one layer are pulled into the layer disposed thereunder in the direction of the cut. This "crush cut" is preferably performed by a compliant knife, specifically a knife under pre-tension, or at least mounted to yield a small amount. This knife is preferably disposed on a rotating cylinder and when performing the cut, can be positioned under suitable pressure against a counter cylinder over which the web is guided and which forms an anvil for the knife.

In accordance with a further inventive concept of intrinsically independent significance, a recess in the material is provided in a longitudinal end zone of the rear part on both sides in the transverse outboard direction, such that the extension of the rear part in the longitudinal direction at the particular longitudinal side edge of the diaper is less than in the area between the recesses and such that the closures and their mating elements are so disposed respective to the rear part and the front part that when the diaper is applied, the back part extends farther upward than the front part, so the rear part reaches up higher than the front part. Expressed differently, this means that the securing means in the back part and the contact zone in the front part of the diaper are at different distances from the corresponding longitudinal end of the diaper in the back part or front part, respectively: the securing means are farther in the longitudinal direction from the longitudinal end of the rear part of the diaper than the contact zone is from the longitudinal end of the front part.

This creates the impression of a slim product which is configured narrow and long. In fact, a greater longitudinal extension of the diaper can be achieved thereby, for example, if the extension of the back part in the longitudinal direction is advantageously greater than the extension of the front part.

The aforementioned recesses are preferably formed by forming blanks in the diaper or as cut-outs from a laminate comprising the top sheet and the back sheet.

In a further aspect of the inventive concept, an edge of the back part bounding the particular recesses is located at the same height as a transverse edge bounding the front part, as said first edge transitions to a longitudinal side edge of the diaper.

Observing this aspect of the diaper when applied to the user, the transition of the edge bounding the recess to the longitudinal side edge of the diaper, meaning the corner or transition point of the diaper side area (frequently described as the ear), is essentially at the same height as the corresponding corner or transition point of the front part.

In a further aspect of the inventive concept, it is proposed to provide the zone for the fastening elements containing the securing means and the corresponding contact zone with an essentially identical longitudinal extent, so that the user is thereby forced to position the fastening means correctly on the contact zone. A correct fit and correct application of the diaper to the user is thereby achieved.

It furthermore proves to be visually attractive and, with respect to achieving an optimal fit, advantageous when the diaper is applied, if the edge of the back part bounding the particular recess terminates in the transverse direction so that it always merges into the transverse edge bounding the front part or terminates therein. While a section or recess running diagonally to the longitudinal and transverse direction would be conceivable to achieve the effect in accordance with the invention, the preceding embodiment proves advantageous, since a smooth merging of the edge bounding the particular recess and the transverse edge bounding the front part is achieved thereby.

In a further aspect of the invention, a second material recess can be furnished in the front part in a longitudinal end zone on both sides in the transverse direction outboard such that the extension of the front part in the longitudinal direction at the specific longitudinal side edge is less than in the area between the recesses. The corresponding difference in the extension will preferably be much less than in the back part.

Furthermore, it proves to be especially advantageous if fastening elements are used in the back part which have adequate extension in the longitudinal direction of 4 to 10 cm, so that the tension arising when the diaper is closed is introduced uniformly into the back part of the diaper, which has a relatively large longitudinal extension.

BRIEF DESCRIPTION OF THE DRAWING

Additional details and benefits of the invention can be found in the appended claims and the illustrative drawings and the subsequent description of a preferred embodiment of the invention. In the drawings:

DETAILED DESCRIPTION

Figure 1:
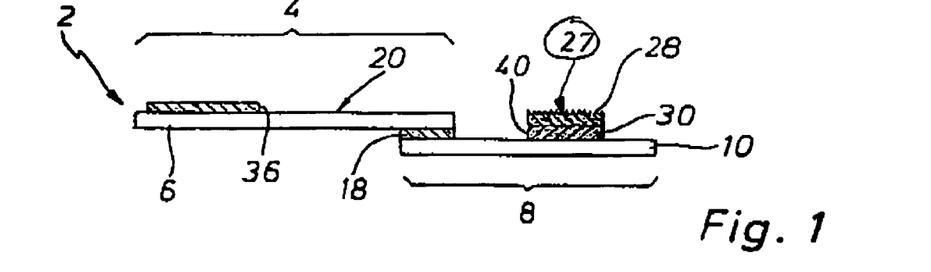
FIG. 1 shows a sectional view of a fastening element for a hygiene article in accordance with the invention.
Figure 2:
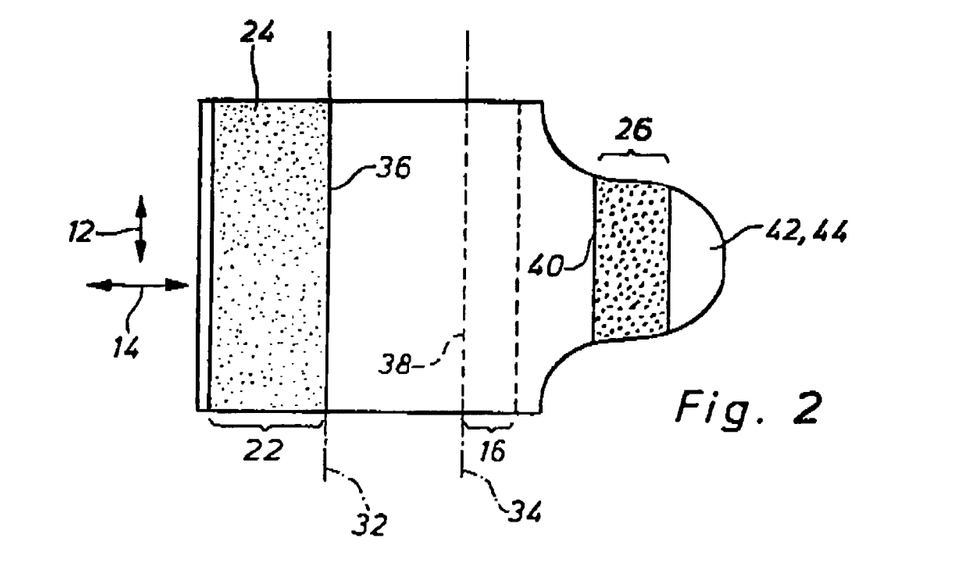
FIG. 2 shows a plan view of the fastening element from FIG. 1.

FIGS. 1 and 2 show a fastening element in accordance with the invention, identified overall as 2. The fastening element 2 comprises a first section 4 of a first supporting layer 6 and a second section 8 of a second supporting layer 10.

The fastening element 2 has been severed as a longitudinal section from a continuous web, where the continuous web extends in a first longitudinal direction. The second section 8 is located in a transverse direction 14 next to the first section 4, where in the instance shown, the first section 4 and the second section 8 overlap one another so that an overlap area 16 is formed to which the two sections 4, 8 are bonded non-detachably by means of a glue 18, by weld spots or in some other fashion.

A first zone 22 which carries an adhesive coating 24 with which the fastening element can be joined to a hygiene article is furnished on a first top side 20 of the first section 4.

Securing means 27 in the form of mechanically acting closures 28, preferably in the form of a hook component of a hook-and-loop material, are furnished in a second zone 26 of the second section 8, specifically adhered by means of a glue 30. The second zone 26 is preferably furnished on the same top side 20 of the fastening element 2 as the first zone 22.

Figure 3:
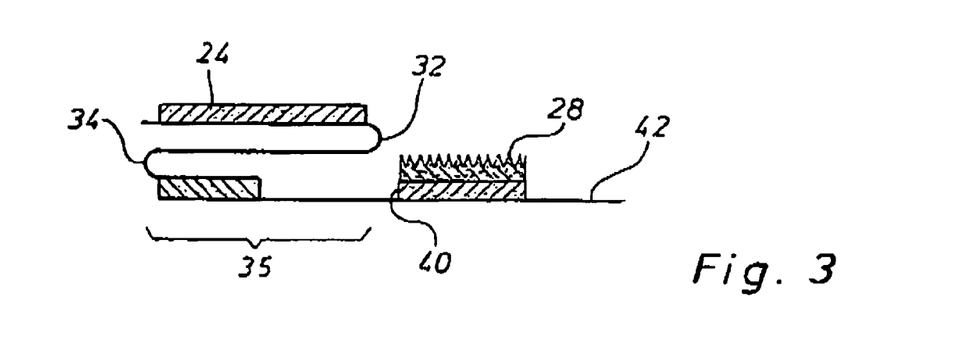
FIG. 3 shows a sectional view of the fastening element from FIGS. 1 and 2 in the folded, Z-shaped configuration.

Furthermore, first and second fold lines 32, 34 are indicated in FIG. 2 and can be seen in FIG. 3 around which the fastening element 2 is folded in a Z-shape in longitudinal direction 12 so that the configuration 35 shown in FIG. 3 is created. Advantageously, the first fold line 32 runs immediately along a longitudinal edge 36 of the adhesive coating 24 in the first zone 22. The second fold line 34 advantageously runs immediately along the material transition between first and second section 4 or 8, along an edge 38 of the overlap area 16.

As can be seen from FIG. 3, the second zone 26 of the second section 8 is spaced apart far enough from the overlap area 16 or from any other material transition area between first section 4 and second section 8 that it is located in the transverse direction 14 outside the folded, Z-shaped configuration 35 of the fastening element 2, which proves advantageous in several respects. In the instance shown, a longitudinal edge 40 of the second zone 26 facing the first section 4, and thus the mechanically acting fasteners 28, extends in the transverse direction almost to the first fold line 36 in the folded, Z-shaped configuration 25. It would also be conceivable that the second zone 26 is positioned with respect to the second section 8 in such a way that the mechanically acting closures 28, or their longitudinal edge 40, are at a distance of a few millimeters from the folded, Z-shaped configuration 35 of the fastening element.

It should be mentioned that the first section 4 is configured elastically extensible in the transverse direction 14 and that the second section 8 is configured essentially not elastically extensible in the transverse direction 14.

It is contemplated that the extension of the fastening element 2 can measure 2 to 10 cm in the longitudinal direction in specific embodiments. If desired or required, the extension of the first section 4 of the fastening element 2 in an elastically configured area between the longitudinal edge 36 of the first zone and the material transition to the second section can measure between about 0.5 to 4.5 cm in the transverse direction, with certain embodiments having a value between about 2 and 3 cm in the transverse direction. Where desired or required, the extension of the second zone of the hygiene article can measure about 0.5 to 2.1 cm in the transverse direction. Where desired or required, it is contemplated that the extension of the pull tab of the fastening element can measure from 0.5 to 2.0 cm in the transverse direction; with the measurement being from 0.7 to 1.2 cm in some embodiments.

An adhesive coating in the first zone 24 and the securing means 27 in the second zone 26 can be applied uninterruptedly and continuously in the longitudinal direction 12 onto a correspondingly continuous web of the first supporting layer 6 and of the second layer 8. In corresponding fashion, the first and second supporting layer 6, 8 are bonded to each other without interruption by a continuous strip of glue 18 or in some other way in the longitudinal direction 12. Simultaneous production of two symmetrically, but offset in the longitudinal direction by $\pi/2$, as known from EP 0 669 121 A1 for example, is also conceivable and advantageous.

When the fastening element with its adhesive application 24 in the first zone 22 is applied to a hygiene article, the second zone 26 with its mechanically acting closures 28 is, as already mentioned, located outside the folded, Z-shaped configuration and can thus serve to affix the fastening element, or the second section 8, to a textile surface of a hygiene article. This is explained in what follows, making reference to FIG. 4.

Figure 4:
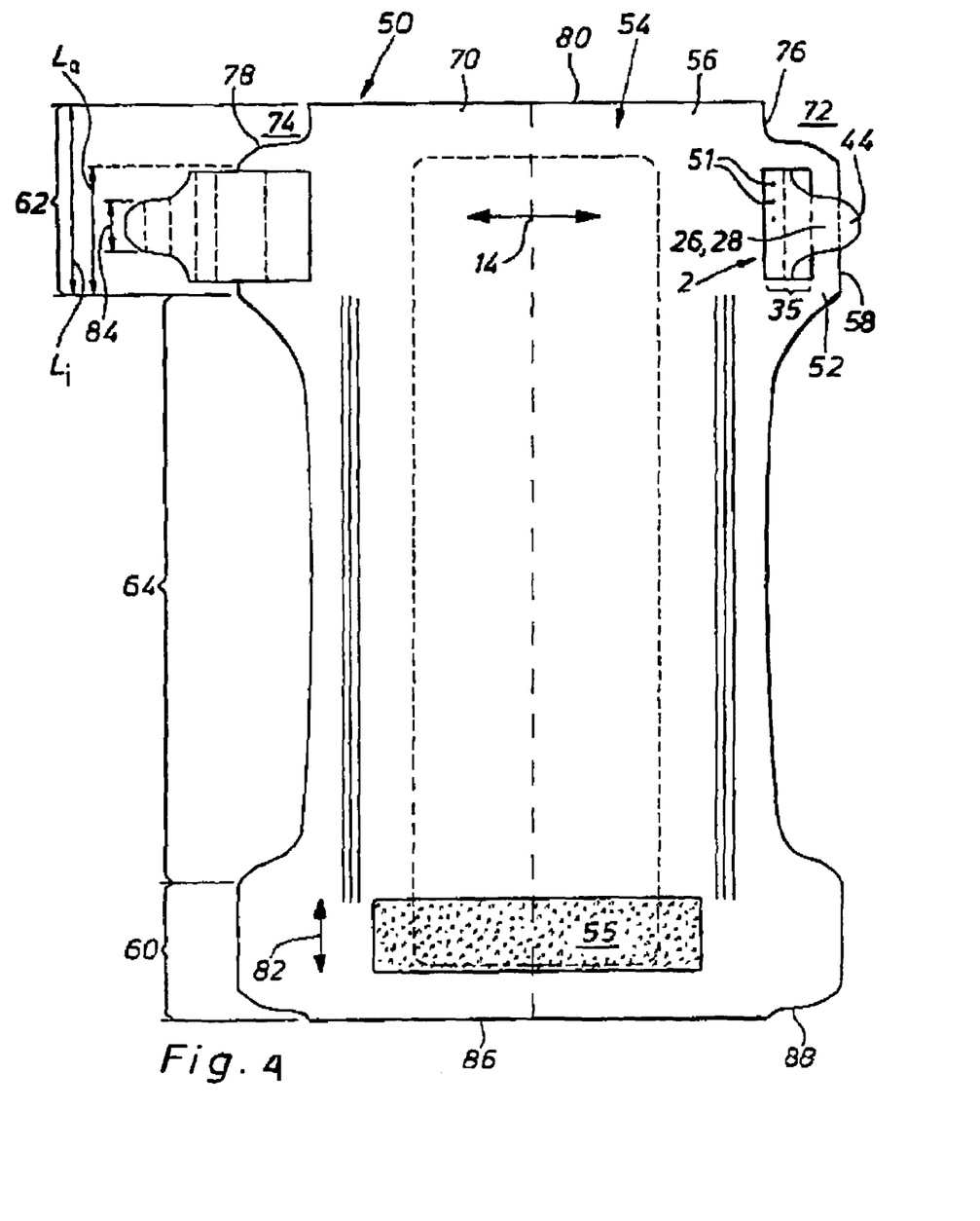
FIG. 4 shows a plan view of a hygiene article in accordance with the invention with fastening elements folded over on one side and unfolded on the other side.

The affixing of the second section 8 to the hygiene article is intended to serve only to secure the fastening element during manufacture and packaging until the hygiene article is applied to a user, at which time at the latest this connection is broken. A user reaches with his fingers between the top side of the hygiene article and a free end zone 42 of the second section 8, which then acts as a pull tab 44.

FIG. 4 shows a plan view of a diaper 50 in accordance with the invention with fastening elements 2 disposed on both sides in a back part of the diaper 50, as described in conjunction with FIGS. 1 to 3. On the left side in FIG. 4, the fastening element 2 is shown unfolded and on the right side it is shown folded in a Z-shape. The particular fastening element 2 is affixed non-detachably with its first zone 22 and the rectangular adhesive coating 24 to an outside of a diaper, that is to a top side 54 of a fluid-impervious back sheet 56 of the diaper when used as intended. The top side 54 is formed of a textile-like nonwoven covering of a fluid-impervious film. The back sheet 56 is consequently formed of a nonwoven/plastic film laminate.

The fastening element 2 is located in the transverse direction 14 at such distance from a longitudinal edge 58 of the diaper 50 in the side flap or ear area of the diaper 50 that only its pull tab projects beyond the longitudinal edge 50 in the transverse direction 14. Care is taken in particular that the second area 26 in which the mechanically acting closures 28 are provided (in the Z-shaped fold of the fastening element) does not project, or projects very little, 5 mm at the most, beyond the longitudinal edge 58 in the transverse direction 14. This prevents the closures 28 from becoming caught when the side flap or ear areas are folded onto the body facing top sheet layer and related damage from occurring.

As can be seen from FIG. 4 in conjunction with FIG. 3, the second zone 26 with the closures 28 is located outside the folded, Z-shaped configuration 35 and thus lies against the top side 54 of the back sheet 56 of the diaper 50. The mechanically acting closures 28 form a releasably adhering connection to the textile-like top side 54 and keep the fastening element 2 in its folded, Z-shaped configuration 35. In particular, this prevents the second section 8 with the zone 26 from becoming detached from the top side 54. In this way manageability of the hygiene article is improved after the fastening elements 2 are attached and they remain in their installed position. The diaper 50 can be handled in the production machinery, in particular folded, stacked and taken for packaging.

The unfolded state of the fastening elements 2 is shown on the left in FIG. 4. To obtain this, a user grasps the pull tab and with the other hand he holds a longitudinal edge area 52 of the diaper 50 and pulls the two components apart. The releasably adhering connection of the closures 28 to the textile-like top surface 54 is broken, and the fastening elements 2 assume the shape shown on the left in FIG. 4 as the folded, Z-shaped configuration 35 unfolds. To apply the diaper 50 to a user, the fastening elements can now be brought to a contact zone 55 in the form of a loop material in the front part of the diaper 50 and attached thereto.

To further secure the fastening elements 2 in a folded, Z-shaped configuration 35, it is conceivable to provide discrete attaching points, such as weld spots 51, which releasably join together the layers of the fastening element 2 folded in a Z-shape over on each other. However, it has been shown that the folded, Z-shaped configuration 35 can be secured in a way which satisfies requirements when the longitudinal sections forming the specific fastening elements are severed from a continuous web; fibers are pulled from the layers disposed above one another in the Z-shape into the layer lying thereunder, so that a form of needling effect is achieved which secures the Z-shaped configuration 35 releasably to itself.

Figure 5:
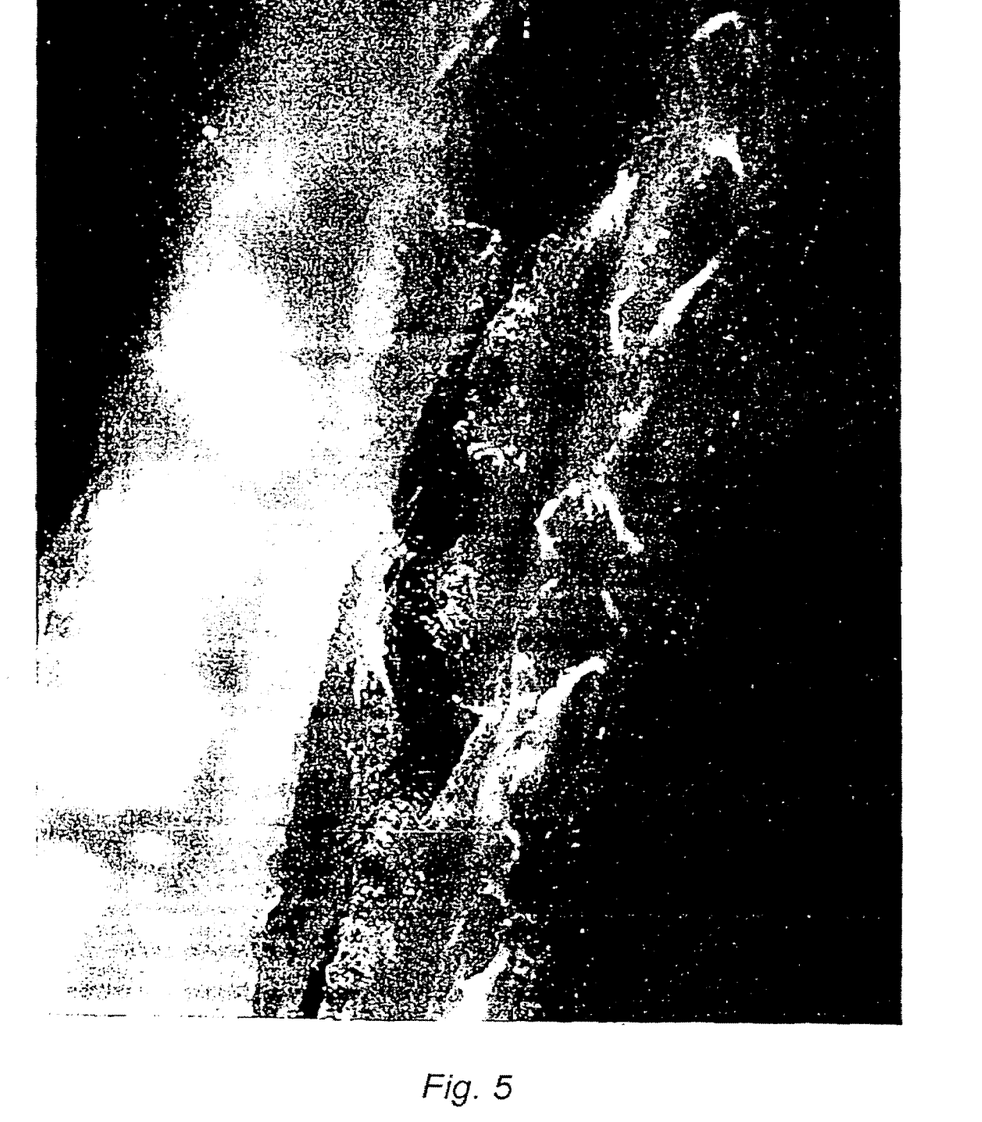
FIG. 5 shows a photographic rendering of the cut edge of the folded, Z-shaped fastening element observed in an epimicroscope.
Figure 6:
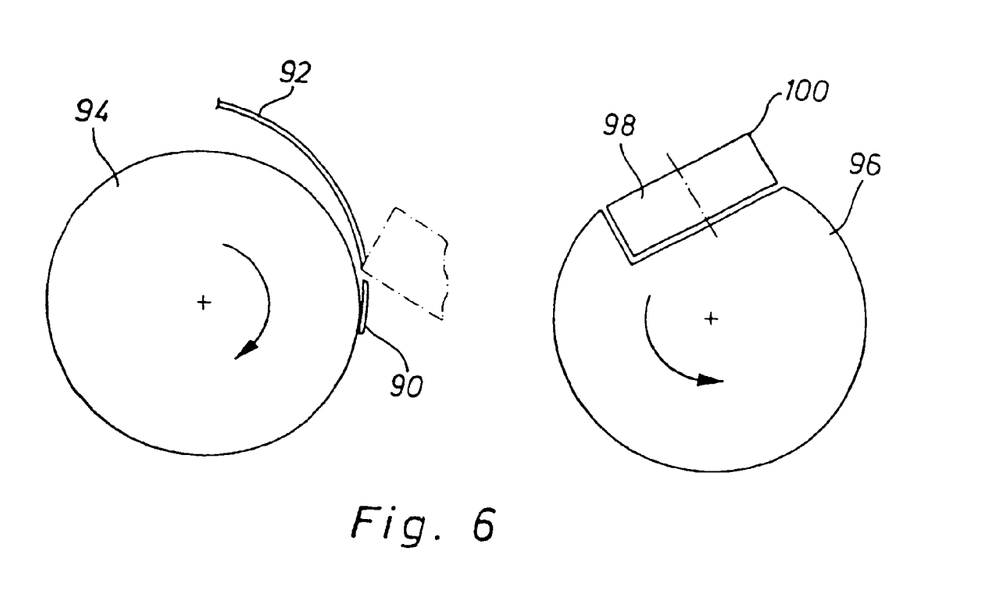
FIG. 6 is a schematic representation of a cutting device for severing individual folded, Z-shaped fastening elements

FIG. 5 shows a schematic outline for a cutting device for severing longitudinal sections 90 from a continuous web 92 which already has the folded, Z-shaped configuration for creating the fastening elements. The cutting device comprises an anvil cylinder 94 across which the continuous web 92 is passed and a knife cylinder 96 having a knife 98 which is under pre-tension and mounted in a floating manner or is intrinsically compliant, with a cutting edge 100. To perform the cut, the knife cylinder 96 is positioned opposite the anvil cylinder 94 in such a manner that the cutting edge 100 of the knife 98 touches the surface of the anvil cylinder 94 and can retract very slightly. The continuous web 92 is thus contacted over a relatively short circumferential area by the cutting edge 100 of the knife 98. In contrast to merely shearing, when a "crush cut" is performed, fibers of the layers overlaid on each other are hereby deflected out of one layer and pulled, crushed or worked into the layer thereunder, so that in the severed longitudinal section 90 the layers folded over on each other in a Z-shape are at least slightly connected to each other and unintentional unfolding is thereby prevented.

A division into a front part 60 and a back part 62 with a crotch area 64 between them can further be seen from FIG. 4. The crotch area 64 is intended as that area which comprises leg cut-outs 66 to form leg openings when the diaper is applied. In diapers in which no leg cut-outs are provided and whose width or extension in the transverse direction 14 does not change or changes only slightly, the crotch area is defined as that area over whose longitudinal extension the longitudinal edge sections bounding the leg openings run. Front part 60 and back part 62 then adjoin the crotch area 64 in the longitudinal direction 62, the crotch area being symmetrical with respect to a transverse center line 68.

As shown in FIG. 4, a recess in the material 72, 74 is furnished in a longitudinal end zone 70 of the back part 62 outwardly on both sides in the transverse direction 14. The material recess 72, 74 is bounded by an arcuate edge 76 or 78, which first runs diagonally from the longitudinal edge 58 and then inward in essentially a transverse direction 14 and is finally turned in the longitudinal direction 12 and then, essentially in the longitudinal direction, meets essentially perpendicularly a first transverse edge 80 which bounds the back part 62. Because of the recesses 72, 74, the extension $L_a$ in the area of the longitudinal side edge 50 is less than the longitudinal extension $L_i$ in the area between the recesses 72, 74. This creates the impression of a slim diaper.

It proves advantageous that the extension of the fastening elements 2 in the longitudinal direction 12 is about 50% of the longitudinal extension of the entire back part 62, so that the tension generated when the diaper is closed is transferred in a highly uniform manner into the material forming the outside of the diaper.

Figure 7:
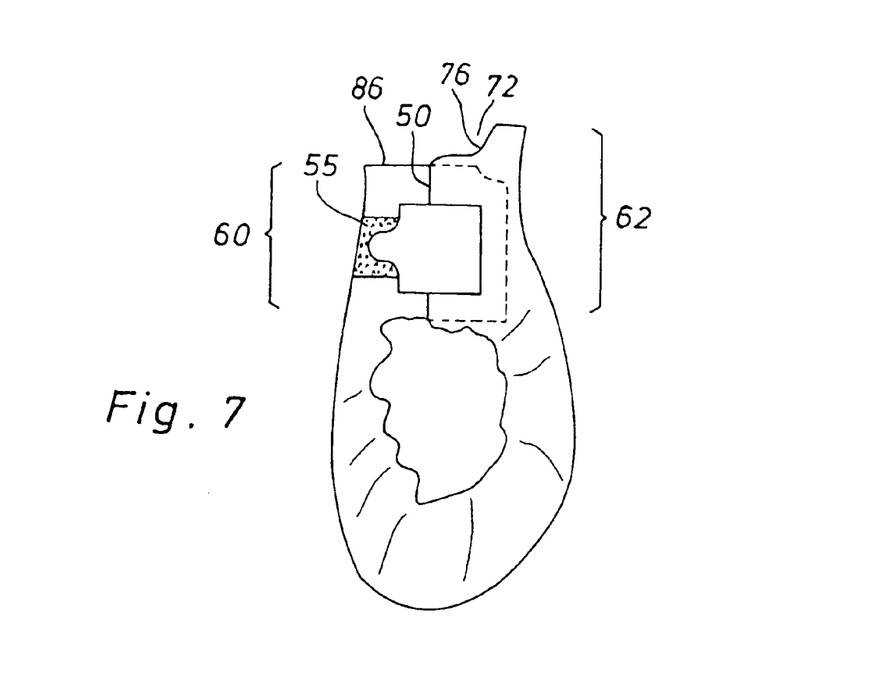
FIG. 7 shows a side view of the diaper in accordance with the invention when worn.

FIG. 4 further shows that the longitudinal extension of the contact zone 55 (indicated by arrow 82) essentially matches the longitudinal extension of the closures 28 of the fastening element 2 (indicated by arrow 84). This obliges the fastening elements 2 in the contact zone 55 to be correctly positioned and thus the diaper to be correctly seated. The fit shown in FIG. 7 from the side then results. It can be seen that the edge 76 bounding the recesses 72, 74 in the transition to the longitudinal side edge 50 of the back part 62 is located at the same height as a second transverse edge 86, which bounds a longitudinal end of the front part 60 of the diaper. Optimal fit of the diaper is thereby achieved. In the instance shown in FIGS. 4 and 7, a less pronounced recess 88 corresponding to recesses 72, 74 is furnished in the front area 60.

However, this is not absolutely necessary.

What is claimed is:

1. A hygiene article, comprising:
a fluid-pervious top sheet;
a fluid-impervious back sheet;
an absorbent core located between the top and back sheets;
fastening elements for releasably closing the hygiene article when applied to a user;
the hygiene article having a first longitudinal direction and a second transverse direction and further having an inside and an outside;
the fastening elements each carrying securing means coacting with a contact zone of the hygiene article, each fastening element having a first zone non-detachably connected to the outside of the hygiene article and a second zone located spaced apart in the transverse direction from the first zone on which the securing means is provided;
the fastening element folded in a Z-shape comprising the first zone with fold lines running in the longitudinal direction; and
the second zone containing the securing means lying outside the folded, Z-shape, wherein the folded Z-shape is secured to itself by one of entwining, crushing, and working fibers from the layers folded on each other in a Z-shape into the layer disposed thereunder when longitudinal sections are severed from a continuous web in the transverse direction.

2. The hygiene article in accordance with claim 1, wherein the fastening element with a zone lying outside the folded, Z-shape is configured to form a releasable retentive connection with a top side of the hygiene article.

3. The hygiene article in accordance with claim 1 wherein the securing means is formed by mechanically acting closures.

4. The hygiene article in accordance with claim 2 wherein the releasable retentive connection is formed by the securing means in the second zone.

5. The hygiene article in accordance with claim 1, wherein the fastening elements are attached to a top side of the hygiene article facing away from the body, and wherein the fastening elements include an adhesive coating interposed between the hygiene article and the fastening element, the adhesive composed of a material that is non-detachably bonded to the fastening element and the hygiene article.

6. The hygiene article in accordance with claim 5, wherein the top side has a textile-like surface formed by a plastic film/nonwoven laminate which comprises the fluid-impervious back sheet.

7. The hygiene article in accordance with claim 1, wherein the folded, Z-shaped fastening elements are positioned in the transverse direction respective to a longitudinal edge of the hygiene article such that the second zone carrying the particular securing means is located at least almost entirely inside the longitudinal edge.

8. The hygiene article in accordance with claim 1, further comprising a pull tab configured to be grasped with a user's finger, the pull tab positioned in the transverse direction outside the second zone of the particular fastening element and on the side of the second zone facing away from the folded configuration, wherein the pull tab extends contiguously from the second zone.

9. The hygiene article in accordance with claim 8, wherein the pull tab of the particular fastening element projects beyond a longitudinal edge of the hygiene article in the transverse direction.

10. A hygiene article having a rear portion, a central portion and a front portion, the hygiene article comprising:
a fluid-pervious top sheet;
a fluid-impervious back sheet;
an absorbent core located between the top and back sheets;
fastening elements for releasably closing the hygiene article when applied to a user, the fastening elements configured to connect the rear portion together with the front portion for releasably closing the article when applied to the user;
the hygiene article having a first longitudinal direction, and a second transverse direction;
the hygiene article having an open state with the rear portion and the front portion unconnected by the fastening elements but being detached from one another and the fastening elements being attached only by one of the rear and front portions, and the hygiene article defining a releasable closed state applied to the user with the rear portion and the front portion being connected by fastening elements,
the fastening elements each carrying securing means coacting with a contact zone of the hygiene article, each fastening element having a first zone with which it is configured to be a non-detachable attachment to the hygiene article and a second zone located spaced apart in the transverse direction from the first zone and in which the securing means is provided;
when the hygiene article is in the open state, the fastening element is folded in a Z-shape with fold lines running in the longitudinal direction and the second zone containing the securing means lying outside the folded Z-shape;
wherein the fastening element has a first section of a first supporting layer and a second section of a second supporting layer, which is disposed next to the first section in the transverse direction and connected thereto, the first section having the first zone and the second section having the second zone forming a free end of the fastening element prior to releasably closing the hygiene article; and
wherein the first and second sections of the fastening element are overlapped in the transverse direction to form an overlap area, the first and second sections joined in the overlap area.

11. The hygiene article in accordance with claim 10, wherein a fold line of the fastening element running in the longitudinal direction runs at least in sections along a material transition between first and second section.

12. The hygiene article in accordance with claim 11, wherein the fold line runs immediately along a longitudinal edge of the second section.

13. The hygiene article in accordance with claim 10, wherein a first fold line of the fastening element runs in the longitudinal direction immediately along a longitudinal edge of the first zone.

14. The hygiene article in accordance with claim 13 wherein a second fold line of the fastening element runs in the longitudinal direction immediately along a longitudinal edge of the second section.

15. The hygiene article according to claim 14 comprising an adhesive coating located in the first zone, the adhesive coating having a longitudinal edge, wherein the first fold line runs immediately along a longitudinal edge of an adhesive coating in the first zone.

16. The hygiene article in accordance with claim 10, wherein the second supporting layer of the fastening element includes an essentially inelastic material and is configured essentially non extensible in the transverse direction.

17. The hygiene article in accordance with claim 16, wherein the first supporting layer of the fastening element comprises a material elastically extensible in at least the transverse direction.

18. The hygiene article in accordance with claim 10, wherein the first zone is configured adhesively.

19. The hygiene article from claim 10, wherein the folded, Z-shape is secured to itself by a plurality of attaching points with a cross-sectional area, each of less than 1 mm$^2$.

20. The hygiene article in accordance with claim 8, wherein the pull tab of the fastening element is formed by a non-adhesive supporting layer.

21. The hygiene article in accordance with claim 1, wherein the extension of the fastening element measures about 2-10 cm in the longitudinal direction.

22. The hygiene article in accordance with claim 10, wherein the extension of the first section of the fastening element in an elastically configured area between the longitudinal edge of the first zone and the material transition to the second section measures about 0.5-4.5 cm in the transverse direction.

23. The hygiene article in accordance with claim 10, wherein the extension of the second zone of the hygiene article having the securing means measures about 0.5-2.1 cm in the transverse direction.

24. The hygiene article in accordance with claim 10, wherein the extension of the pull tab of the fastening element measures 0.5-2.0 cm in the transverse direction.

25. The hygiene article in accordance with claim 10, wherein the extension of the specifically adhesively configured first zone of the fastening element in the transverse direction essentially corresponds to the width of the folded, Z-shape.

26. The hygiene article in accordance with claim 10, wherein the first zone and the second zone are provided on the same side of a continuous web.

27. The hygiene article in accordance with claim 1, wherein the extension of the fastening element measures about 5-7 cm in the longitudinal direction.

28. The hygiene article in accordance with claim 10, wherein the extension of the first section of the fastening element in an elastically configured area between the longitudinal edge of the first zone and the material transition to the second section measures about 2-3 cm in the transverse direction.

29. The hygiene article in accordance with claim 10, wherein the extension of the second zone of the hygiene article having the securing means measures about 1-1.5 cm in the transverse direction.

30. The hygiene article in accordance with claim 10, wherein the extension of the pull tab of the fastening element measures 0.7-1.2 cm in the transverse direction.

31. A hygiene article having an inside, an outside, a rear portion, a middle portion, and a front portion, the hygiene article comprising:

a fluid-pervious top sheet;

a fluid-impervious back sheet;

an absorbent core located between the top and back sheets:

fastening elements for releasably closing the hygiene article when applied to a user, the fastening elements configured to connect the rear portion together with the front portion configured for releasably closing the article when applied to the user, the fastening elements non-detachably connected to the outside of the hygiene article;

the hygiene article having a first longitudinal direction and a second transverse direction;

the hygiene article having an open state with the rear portion and the front portion unconnected by the fastening elements but being detached from one another and the fastening elements being attached only by one of the rear and front portions, and the hygiene article defining a releasable closed state applied to the user with the rear portion and the front portion being connected by fastening elements, the fastening elements each carrying securing means coacting with a contact zone of the hygiene article; each fastening element having a first zone with which it is configured to be a non-detachable attachment to the hygiene article and a second zone located spaced apart in the transverse direction from the first zone and in which the securing means is provided;

when the hygiene article is in the open state, the fastening element is folded in a Z-shape with fold lines running in the longitudinal direction; and the second zone containing the securing means lying outside the folded Z-shape, wherein the securing means is formed by mechanically acting closures.

* * * * *